(12) United States Patent
Barthold

(10) Patent No.: US 11,826,271 B2
(45) Date of Patent: Nov. 28, 2023

(54) INTRALUMINAL VASCULAR PROSTHESIS

(71) Applicant: JOTEC GmbH, Hechingen (DE)

(72) Inventor: Franz-Peter Barthold, Balingen (DE)

(73) Assignee: JOTEC GmbH, Hechingen (DE)

( * ) Notice: Subject to any disclaimer, the term of this patent is extended or adjusted under 35 U.S.C. 154(b) by 0 days.

(21) Appl. No.: 16/737,515

(22) Filed: Jan. 8, 2020

(65) Prior Publication Data

US 2020/0138611 A1    May 7, 2020

Related U.S. Application Data

(63) Continuation of application No. PCT/EP2018/069123, filed on Jul. 13, 2018.

(30) Foreign Application Priority Data

Jul. 14, 2017 (DE) ............... 10 2017 115 898.7

(51) Int. Cl.
*A61F 2/07* (2013.01)
*A61F 2/06* (2013.01)
(Continued)

(52) U.S. Cl.
CPC .............. *A61F 2/91* (2013.01); *A61F 2/07* (2013.01); *A61F 2/89* (2013.01); *A61F 2/856* (2013.01);
(Continued)

(58) Field of Classification Search
None
See application file for complete search history.

(56) References Cited

U.S. PATENT DOCUMENTS

| | | | |
|---|---|---|---|
| 2008/0114446 A1* | 5/2008 | Hartley | A61F 2/07 623/1.13 |
| 2008/0208213 A1 | 8/2008 | Benjamin et al. | |

(Continued)

FOREIGN PATENT DOCUMENTS

| | | |
|---|---|---|
| CN | 105142571 A | 12/2015 |
| CN | 205729569 U | 11/2016 |

(Continued)

OTHER PUBLICATIONS

International Preliminary Report on Patentability for International Application No. PCT/EP2018/069123, dated Jan. 23, 2020.
(Continued)

*Primary Examiner* — Leslie Lopez
(74) *Attorney, Agent, or Firm* — Jason H. Vick; Sheridan Ross, PC

(57) ABSTRACT

The present invention relates to an intraluminal vascular prosthesis for implantation into a blood vessel, with a stent framework and a prosthesis material secured onto the stent framework, wherein the vascular prosthesis has a hollow-cylindrical body with a lumen passing there through and a circumferentially closed jacket, wherein at least one substantially U-shaped or V-shaped fenestration-cut in the prosthesis material of the vascular prosthesis is provided, which is dimensioned and formed, such that via the fenestration-cut a flap-like access to the lumen of the vascular prosthesis for at least one side branch branching off from the hollow-cylindrical body can be formed.

14 Claims, 2 Drawing Sheets

(51) Int. Cl.
*A61F 2/856* (2013.01)
*A61F 2/91* (2013.01)
*A61F 2/89* (2013.01)
*A61F 2/82* (2013.01)

(52) U.S. Cl.
CPC ... *A61F 2002/061* (2013.01); *A61F 2002/075* (2013.01); *A61F 2002/823* (2013.01); *A61F 2230/0013* (2013.01); *A61F 2230/0054* (2013.01); *A61F 2250/0098* (2013.01)

(56) References Cited

U.S. PATENT DOCUMENTS

| | | |
|---|---|---|
| 2009/0264977 A1 | 10/2009 | Bruszewski et al. |
| 2013/0074849 A1 | 3/2013 | Rousseau et al. |
| 2013/0282102 A1* | 10/2013 | Peterson .................. A61F 2/07 623/1.13 |
| 2014/0277347 A1 | 9/2014 | Daugherty et al. |
| 2014/0358221 A1 | 12/2014 | Ho et al. |
| 2018/0116783 A1* | 5/2018 | Kratzberg ................. A61F 2/07 |

FOREIGN PATENT DOCUMENTS

| | | |
|---|---|---|
| EP | 2522306 A2 | 11/2012 |
| EP | 3315092 A2 | 5/2018 |
| JP | 2010-508970 A | 3/2010 |
| JP | 2016-511058 A | 4/2016 |
| WO | WO 2008/057568 A1 | 5/2008 |
| WO | WO 2009/064672 | 5/2009 |
| WO | WO 2014/149531 A1 | 9/2014 |
| WO | WO 2016/109738 A2 | 7/2016 |

OTHER PUBLICATIONS

International Search Report for International Application No. PCT/EP2018/069123, dated Oct. 18, 2018.
Written Opinion for International Application No PCT/EP2018/069123, dated Oct. 18, 2018.
Office Action (Including Translation) for corresponding Chinese Patent Application No. 201880046375.8, dated Nov. 17, 2021.
Office Action for corresponding Chinese Patent Application No. 201880046375.8, dated May 7, 2022.
Notice of Reasons for Refusal (Including Translation) for corresponding Japanese Patent Application No. 2020-501276, dated Jun. 28, 2022.

* cited by examiner

INTRALUMINAL VASCULAR PROSTHESIS

CROSS REFERENCES TO RELATED APPLICATIONS

This application is a continuation of international patent application PCT/EP2018/069123, filed on Jul. 13, 2018, designating the U.S., which international patent application has been published in German language and claims priority from German patent application DE 10 2017 115 898.7, filed on Jul. 14, 2017. The entire contents of these priority applications are incorporated herein by reference.

BACKGROUND

The present invention relates to an intraluminal vascular prosthesis for implantation in a blood vessel, with a stent framework and a prosthesis material secured onto the stent framework, wherein the vascular prosthesis has a hollow-cylindrical body with a lumen leading there through and a circumferentially closed jacket.

Intraluminal vascular prostheses—also referred as endovascular stent/stent grafts—are generally known in the art. They are implanted in arteries for the treatment of aneurysms. These are vascular prostheses which are generally used to support unstable, brittle or thrombotic vessel walls. For a treatment, a vascular prosthesis is released at the diseased or damaged region of the vessel, thus restoring the functionality of the original vessel or supporting the still existing integrity of the vessel.

Here, but also in general, an aneurysm is understood as a widening or bulging of an arterial blood vessel as a consequence of congenital or acquired lesions of the wall. Lesions of the wall arise, for example, due to very rapid growth of the vessels. For example, a person's aorta grows for life, thus the diameter of the aorta is 20-30% larger in 70-year-olds than in 20-year-olds. 75% of all aneurysms are located in the abdominal aorta. The bulge in this case can affect the vessel wall as a whole or, in what is called a false aneurysm or dissection, blood flows from the lumen of the vessel in between the layers of the vessel wall and tears these apart from one another. Non-treatment of an aneurysm may lead to a rupture of the artery in advanced stages, after which the patient suffers internal bleeding.

Further causes of a thoracic and thoraco-abdominal aortic aneurysm may be arteriosclerosis, high blood pressure and inflammation processes of the vessel wall. Injuries of the thorax due to serious accidents may also lead to an acute or chronic aortic aneurysm.

For the treatment of aneurysms, the affected arteries are stabilized—according to the state of the art—by implantation of a stent or stent graft to prevent rupture of the vessel. A wide variety of vascular prostheses are used depending on the type of application. In general, a distinction is made between balloon-expandable and self-expanding systems and such without or with prosthetic material. The latter are also referred as "covered" stents. The prosthetic material is often made of textile or polymer film, and in particular prevents the passage of blood or of blood components or deposits through the wall of the vascular prosthesis, as well as the inward growth of tissue through the wall into the interior of the vascular prosthesis. With this design, the stress on the vessel wall at the implantation site of the stent graft is relieved and possible embolisms at these regions are prevented.

The tubular metal frame, of which the lateral surface may be covered by a textile or polymer film, is shaped such that a hollow-cylindrical body is obtained. The metal frame is usually made of a wire mesh or of meandering stent elements arranged one behind the other, which are also referred as stent springs, which are optionally connected to one another by connecting struts or which are merely connected to one another via the prosthesis material. In case of a self-expanding vascular prosthesis, the wire mesh or the stent elements are made of a shape memory material or shape memory alloy, e.g. nitinol.

For implantation, the vascular prosthesis is radially compressed, such, that its cross-sectional area decreases considerably. For this purpose the vascular prosthesis is first introduced into a sleeve, also referred to as a sleeve catheter. The sleeve catheter is part of the delivery system with with the vascular prosthesis is advanced to the region of the aneurysm, where the vascular prosthesis is released. The position of the vascular prosthesis is usually monitored via X-ray markers, such that the vascular prosthesis can be adjusted if necessary. Due to the resilience of the metal frame/framework, the vascular prosthesis expands again to its original shape, and, in doing so, stretches its lateral/jacket surface, which gets anchored inside the blood vessel proximally and distally in relation to the aneurysm. In this way, the blood now flows through the vascular prosthesis, preventing further stressing of the bulge. The vascular prosthesis remains fixed in position at the desired location in the vessel due to its outward pressing. The expansion of the metal frame can be achieved by using self-expanding metal such as nitinol, or, in the case of balloon-expandable vascular prostheses, by using a dilatation balloon which is inserted into the metal frame from the inside and whose dilatation expands the metal frame.

It is often problematic that the blood vessel to be treated has further lateral blood vessels. If a vascular prosthesis is implanted in such a vessel, the side blood vessels would be cut off from the blood supply by the blood-tight prosthesis material. This problem is solved by so called "fenestrations" which are located in the prosthetic material. Fenestrated vascular prostheses are those that have preformed holes (fenestrations) to allow one or more vascular branches branching off the vascular prosthesis.

Further, vascular prostheses are known, in which the fenestration is introduced in situ, i.e., after the vascular prostheses have been positioned in the vessel. Such a vascular prosthesis is known, for example, from WO 2009/064672 A2. Here, the main stent graft is penetrated in situ with a needle to form a needle hole in the graft material. Then, a dilator assembly is pushed through the needle hole to expand the needle hole. A particular disadvantage of these vascular prostheses is that the prosthesis material is torn or injured at the intended positions in order to form the fenestrations. This may result in a further tearing of the prosthesis material, so that the fenestration expands uncontrolled, which in turn can lead to uncontrolled outflow of blood in this region of the vascular prosthesis. A further disadvantage of known prostheses and methods is that the location of the side vessel cannot be localized with contrast agents.

The disadvantages of vascular prostheses known in the state of the art are that they must be positioned highly precisely in relation to the off-branching vessels, otherwise a bulge may form in the region of the holes, while the side vessels are cut off from the blood supply. This requires a lot of experience from the attending physician.

Particularly in case of vascular prostheses, which are intended to bridge several side vessels, it is usually necessary to provide vascular prostheses that are precisely tailored to the respective patient or his/her vessel if successful treatment is to be achieved. This is particularly cost-intensive and time-consuming, since the vessel to be treated must first be examined for its exact nature.

Furthermore, state-of-the-art vascular prostheses are known which have lattice-like fenestrations in the prosthesis material through which side branches can be placed. These "mini-fenestrations" are used to form temporary endo-leaks, since these "holes" in the tissue allow the blood to leak for a certain period of time in order to even allow an examination of the off-branching tissue. In these models, many small "holes" or fenestrations are distributed over a portion of the prosthesis. After in-situ fenestration, the remaining, and then un-used holes should be closed by blood coagulation and terminate the endoleakage.

However, these endoleakages are already a disadvantage per se, since via these blood leaks out of the prosthesis in an uncontrolled manner. Furthermore, these lattice-/sieve-like fenestration holes may not be formed too large, otherwise the endoleakage will be too large either. However, this has the disadvantage that there is a risk of the material tearing when positioning larger side branches.

Therefor, an object of the present invention is to provide for an intraluminal vascular prosthesis or a stent graft with which the above-described disadvantages can be overcome and to provide for vascular prostheses which are flexible, i.e. do not need to be custom-made, while maintaining the dimensions of the fenestrations.

SUMMARY

According to one embodiment, an intraluminal vascular prosthesis for implantation into a blood vessel is provided, with a stent framework and a prosthesis material secured onto the stent framework, wherein the vascular prosthesis has a hollow-cylindrical body with a lumen passing there through and a circumferentially closed jacket characterized in that at least one substantially U-shaped or V-shaped fenestration-cut in the prosthesis material of the vascular prosthesis is provided, which is dimensioned and formed, such, that via the fenestration-cut a flap-like access to the lumen of the vascular prosthesis for at least one side branch branching off from the hollow-cylindrical body can be formed.

With the intraluminal vascular prosthesis according to the invention, a vascular prosthesis is provided which can be used to support unstable, brittle or thrombotic vessel walls and in particular to treat vessels affected by aneurysms. This is achieved by the special configuration of the vascular prosthesis according to the invention, especially by the flap-like access: The flaps only open outwards at those positions where a side vessel is actually in the vicinity or immediately adjoins it. The other flaps remain closed due to the wall contact, and, thus reduce the risk of unwanted endoleaks.

Another advantage is that the opening of the flaps can be formed much larger than those of lattice/sieve-like fenestration holes, as described above. This, in turn, reduces the risk of the prosthesis material tearing out.

Here, and generally in the present description, "substantially" means that the U- or V-shaped fenestration-cut does not need to have the exact shape of the letter U or V, but that it also includes shapes which a skilled person will recognise and classify as approximately U- or V-shaped.

The fenestration-cut, and thus, the flap-like access, enables the blood supply to the side vessels to be maintained. The vascular prosthesis is released in the vessel such that at least one flap-like access faces to the side vessel. A particular advantage is that the blood supply can be achieved by simply flipping open/opening the access. The prosthesis material, which is located within the U- or V-shaped fenestration-cut, is pressed against the vessel wall of the side branch due to the blood flow. Also, via the flap-like access, another vascular prosthesis can be released. This also ensures the supply of the side vessels.

In addition, the vascular prosthesis according to the invention offers the advantage that the vascular prosthesis can have considerably more fenestration-cuts than the vessel has side vessels. In the implanted state the flap-like accesses are in contact to the vessel wall, wherein no blood is flowing out through the opening. The flap can therefore only open by itself as long as there is a side branch of a side vessel behind/directly adjacent to the flap. The flap can therefore be easily pushed opened at the desired positions in the vessel and remains closed at those sites where there is no side branch. This special configuration also enables targeted clogging.

Furthermore the special configuration of the vascular prosthesis according to the invention minimizes the risk of endoleaks. An endoleak refers to a leak between an implanted prosthesis and the aneurysm bag. At 15%, endoleak is the most common complication after endovascular treatment of an aortic aneurysm. The blood flow in the aneurysm bag persists if the aneurysm is only incompletely shut off. There is still a risk of expansion and a risk of rupture.

Thus, the vascular prosthesis according to the invention has the advantage that, on the one hand, it can be produced to fit every patient individually, i.e. it has as many fenestration-cuts as the vessel has side vessels, but, on the other hand, the vascular prosthesis can also be made in a standardized way such that it can be used universally, with a large number of fenestration-cuts.

The stent framework according to the invention can be single stent-elements, which can be connected to each other or with each other, or can be net-like wire meshes. On the one hand, the stent framework serves to fix the prosthesis material, on the other hand, the stent-framework gives of the vascular prosthesis a hollow-cylindrical structure. In addition, the stent framework keeps the vascular prosthesis in position within the vessel by pressing the vascular prosthesis against the vessel wall in the implanted state.

In the present case, "hollow-cylindrical body" means the body of the vascular prosthesis, which is made of a stent framework and at least partially of prosthesis material. The stent framework can be made of individual stent elements.

According to an embodiment, it is preferred if the intraluminal vascular prosthesis has between one and nine fenestration-cuts on at least one circumferential portion U.

Thus, according to the invention, 1, 2, 3, 4, 5, 6, 7, 8 or 9 fenestration-cuts may be present which are distributed over at least one circumferential portion U of the vascular prosthesis. A larger number of fenestration-cuts over a certain circumferential portion of the vascular prosthesis according to the invention has the advantage that the exact releasing of the vascular prosthesis in relation to its exact circumference in the vessel is not critical, since a larger number of flaps increases the probability that one of the flaps or at least one of the flaps will be released over the branched vessel. Due to the special flap-like configuration of the fenestration-cuts, the access remains closed if the prosthetic material of the fenestration-cut is released directly on/vis-à-vis the vessel wall. The more fenestration-cuts a vascular prosthesis has, the easier the implantation and, if necessary, the releasing of the side branches can be.

Depending on the nature of the vessel in which the intraluminal vascular prosthesis is to be released, it may be necessary for the vascular prosthesis to have several circumferential portions, each of which in turn has between 1, 2, 3, 4, 5, 6, 7, 8 or 9 fenestration-cuts.

The fenestration-cuts can be available in different sizes. The length of the fenestration-cut or the resulting diameter of the flap-like access is preferably adapted to the diameter of the side branches.

A "circumferential portion" U of the vascular prosthesis according to the invention is a circumferential surface portion of the vascular prosthesis, i.e. a cylindrical portion over which the at least one fenestration section is distributed.

According to an embodiment of the invention, it is preferred if in the vascular prosthesis, which comprises meandering circumferential stent-rings arranged one behind the other, which are not connected to one another and which comprises a prosthesis material onto which the stent-rings are secured, the circumferential portion is defined by the prosthetic portion formed between two stent rings arranged one behind the other.

According to another embodiment, the circumferential portion is preferably between 10 mm and 40 mm, preferably between 10 and 20 mm.

According to the invention and according to another embodiment the vascular prosthesis has between 1, 2, 3, 4, 5, 6, 7, 8 or 9 fenestration-cuts provided in between 1, 2, 3, 4, 5, 6, 7, 8, 9 or 10 circumferential portions.

According to an embodiment that has several, i.e. at least two, circumferential portions, these can either have a different number of fenestration-cuts or the same number of fenestration-cuts. Also, the fenestration-cuts of a first circumferential portion can be the same or different in length to the fenestration-cuts of a circumferential portion, as well as the same or different in length within a first and/or second circumferential portion. It is further understood that a circumferential portion can have several, i.e. at least two, equally long fenestration-cuts, as well as at least one further different fenestration-cut.

According to another embodiment the stent framework of the intraluminal vascular prosthesis is made of rings of meandering circumferential struts arranged one behind the other in its longitudinal direction, but not connected to one another.

A "meandering formation" is understood here to mean any loop-shaped course of a stent element. In the present case, "stent" or "stent element" or "stent ring" denotes any structure which gives a vascular prosthesis an expansion force and/or a supporting function. Accordingly, a stent element is therefore any element that has the properties of a stent.

In the present case, a "stent spring" is understood to mean any one-piece, annular element that can be compressed on account of its material and can expand again like a spring after removal of the compression pressure. The stent springs have an undulating profile, wherein wave peak and wave valley form a phase and alternate with each other.

The stent elements or stent springs can have the same or different circumferential amplitudes, which result from the legs of the stent springs having identical lengths or different lengths. Amplitudes of different length afford the advantage that the stent graft can be adapted to the respective vessels and to the respective circumstances (curvatures, branch vessels, constrictions, etc.).

According to the invention, the stent elements can also comprise braided, twisted or laser-cut stent elements instead of the individual stent springs.

In this embodiment the individual meandering circumferential struts are preferably connected via the prosthesis material. For this purpose, the meandering circumferential struts can be secured to the prosthesis material with a seam. The struts can be arranged on the prosthesis material in such a way that there is an un-stented region on the prosthesis material.

Surgical thread is preferably used as the sewing material. This surgical thread is preferably made of polyester, polyurethane, polystyrene, polytetrafluoroethylene, ultra-high molecular weight polyethylene (UHMPE), or mixtures thereof.

According to a preferred embodiment the stent framework extends over the entire length of the vascular prosthesis.

Depending on the vessel, it may be necessary for the vascular prosthesis to have a full-lengths stent framework. This can be achieved, for example, by means of a wire mesh, which at least partially has prosthesis material. In the region with the prosthetic material, the fenestration-cuts may be within the forming meshes.

As an alternative to wire mesh, the vascular prosthesis can also have several stent elements connected to each other by connecting elements. This can also be used to form a continuous stent framework.

According to another embodiment the stent framework does not extend over the entire length of the vascular prosthesis such that at least one un-stented region is formed.

This embodiment offers the advantage that depending on the vessel in which the vascular prosthesis is to be implanted, a custom-fit vascular prosthesis can be produced. Therefore, the number and shape of the stent framework or the individual stent elements, the amount of prosthesis material, the diameter of the vascular prosthesis, the material used for the stent framework or the prosthesis material, the number of fenestration incisions, etc. can be varied.

According to another embodiment a respective stent ring at the first and/or second end of the vascular prosthesis is provided, which is optionally connected to the stent framework.

The first or second end according to the invention refers to the proximal or distal end of the vascular prosthesis. In principle, in the case of vascular prostheses, the respective ends are generally referred to by the terms "distal" and "proximal", where the term "distal" designates that part or end lying farther downstream in relation to the blood flow. By contrast, the term "proximal" designates, again in relation to the blood flow, a part or the end lying farther up-stream in relation to the blood flow. To put it another way, the term "distal" means in the direction of the blood flow, and the term "proximal" means opposite to the direction of the blood flow. In the case of catheters, by contrast, or insertion systems, the term "distal" designates the end of the catheter or insertion system that is inserted into the patient, or the end farthest away from the user, and the term "proximal" designates the end nearer to the user.

According to another embodiment the at least one fenestration-cut has a cut length of between 2 mm to 10 mm, preferably between 5 mm and 7 mm.

This embodiment has the advantage that the access formed by the fenestration-cut corresponds to the usual dimensions of the side vessels.

According to another embodiment in case of a plurality of fenestration-cuts they have an same or different length of the cut.

Due to the different nature of the side vessels, differently sized fenestration-cuts are also necessary. While a cut that is too small could still ensure that the blood supply is maintained, an access that is too small could have an unfavourable effect on blood pressure. With this embodiment, both large and small side vessels can be bridged.

According to a further embodiment the intraluminal vascular prosthesis further has, in addition to the hollow-cylindrical body, at least one hollow-cylindrical side body, which is connectable to the vascular prosthesis via the flap-like access.

"At least one hollow-cylindrical side body" refers preferably to one, two, three or four side body/bodies. With the side body, the vascular prosthesis has an opening, whereby the access of the side vessels via the vascular prosthesis side body can be reliably guaranteed. This embodiment is particularly advantageous for vessels in which an injury or rupture is located near a side branch. Therefore, it is advantageous if not only the main vessel but also the side vessels are supported by a first and second vascular prosthesis, respectively.

The vascular prosthesis according to the invention, it is generally understood that the at least one side branch, which is connected to the vascular prosthesis via the flap-like access to the lumen of the vascular prosthesis, can branch both outwards in relation to the vascular prosthesis and inwards into the lumen of the vascular prosthesis.

The hollow-cylindrical side body may be a second vascular prosthesis according to the invention. This second vascular prosthesis can have the same properties as the already described vascular prosthesis. It can therefore be a self-expandable or balloon-expandable vascular prosthesis, which optionally has prosthesis material. In one embodiment, the hollow-cylindrical side body does not have any prosthesis material.

This embodiment therefore offers the advantage that the vascular prosthesis according to the invention can be adapted to the respective anatomical conditions of the patient to be treated.

According to another embodiment a marker is located on the intraluminal vascular prosthesis, which marker contains a radiopaque material or is made entirely of radiopaque material, wherein the marker is provided in particular at the end points of the at least one fenestration-cut and/or along the fenestration-cut.

With the aid of the markers, which are located at specific sites of the vascular prosthesis, it is possible to precisely determine the position of the vascular prosthesis during and after the implantation and to do so very quickly. Markers around/along the fenestration-cut are particularly useful, since the vascular prosthesis should be positioned particularly correctly in this region.

Preferably, the radiopaque markers are made of one or more of the following materials, e.g. gold, palladium, tantalum, chromium, silver, etc. The shape of the markers can be of any kind, for example round, polygonal, and/or for example can have the shape of letters, numbers or figures that are helpful for the orientation of the stent graft in the vessel.

According to an embodiment, a method for treating a vascular disease, for example, an aneurysm, is provided, the method comprising the step of implanting, i.e. inserting and releasing, an intraluminal vascular prosthesis described above into a blood vessel of a patient in need of the treatment.

According to one embodiment, a method for inserting an intraluminal vascular prosthesis into a blood vessel of a patient is provided, with the following steps:

Inserting and releasing the first intraluminal vascular prosthesis in a blood vessel of a patient; and Inserting at least one second vascular prosthesis via the flap-like access formed by the at least one fenestration-cut in the hollow-cylindrical body to form at least one side branch of the intraluminal vascular prosthesis in a side vessel extending from the blood vessel.

T According to one embodiment, a method for enlarging an intraluminal vascular prosthesis is provided, with the following steps:

providing an intraluminal vascular; and guiding through the flap-like access, formed by the at least one fenestration-cut in the hollow-cylindrical body of the intraluminal vascular prosthesis, a second vascular prosthesis to form a side branch vascular prosthesis.

According to one embodiment, a method for producing an intraluminal vascular prosthesis is provided, wherein the fenestration-cut in the prosthesis material is made by means of a thermal treatment of the prosthesis material.

According to a preferred embodiment of the method the fenestration-cut is made by means of a laser instrument or of an apparatus.

This embodiment offers the advantage that particularly precise cuts can be made using a laser instrument. Furthermore, the heating during the cut melts the cut edges of the prosthesis material, such, that the tissue at this position does not fray unwanted or has such sharp edges that the vessel wall may be damaged.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

Illustrative embodiments of the invention are explained in more detail in the following description and shown in the drawing, in which.

EMBODIMENTS

Figure 1:
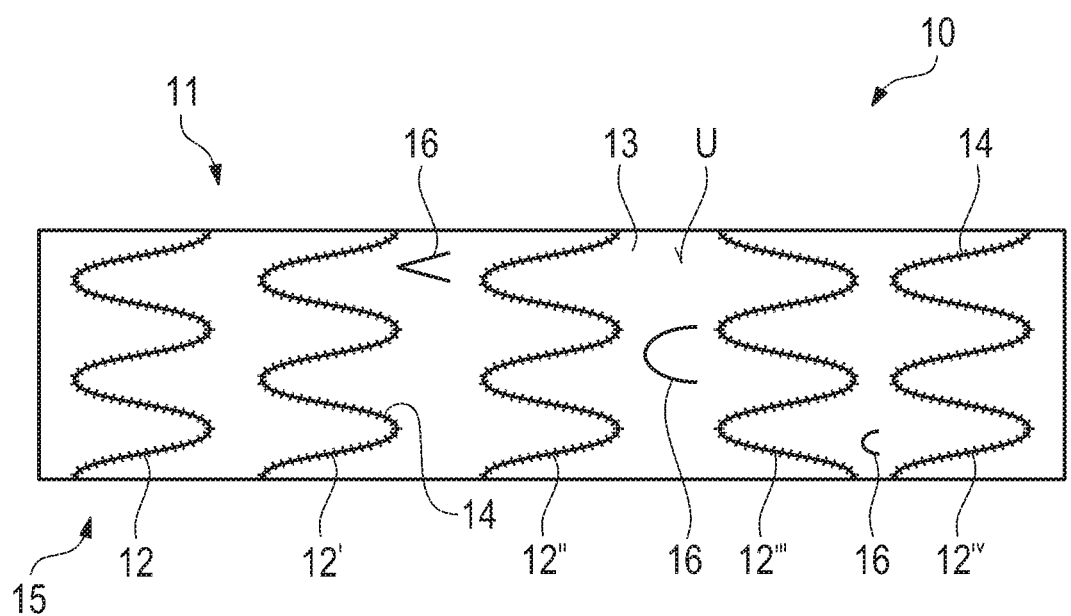
FIG. 1 shows a first schematic view of a detail of an intraluminal vascular prosthesis according to the invention.

FIG. 1 shows a first schematic view of an embodiment of a detail of an intraluminal vascular prosthesis 10 according to the invention, comprising a stent-framework 11, which in turn is formed of individual stent-springs or stent-rings 12, which have rings of meandering circumferential struts. The stent springs/stent rings 12, 12$^I$, 12$^{II}$, 12$^{III}$, 12$^{IV}$ in this figure five in number are secured to the prosthetic material 13 by means of a seam 14. The prosthetic material 13 in this figure extends over the entire vascular prosthesis 10. The stent springs 12 are arranged one behind the other in this embodiment and are not connected to each other, but only via the prosthetic material 13. The stent springs 12 are preferably made of a material or have such a material which is self-expanding. The stent springs 12 can thus change from a compressed state to a relaxed, expanded state. This is preferred in order to be able to implant the intraluminal vascular prosthesis 10 into a vessel.

The prosthesis material 13 is formed as a hollow-cylindrical body 15 with a lumen passing through it, whereby the prosthesis material 13 forms a circumferentially closed jacket. The hollow-cylindrical structure of the body 15 is mainly formed by the stent framework 11. The stent framework 11 can preferably extend over the entire length of the vascular prosthesis 10, as this determines the strength of the structure of the vascular prosthesis 10. Alternatively, the stent framework 11 does not extend over the entire length of the vascular prosthesis 10. Thus, the stent framework 11 is interrupted by prosthesis material 13. In this embodiment, the prosthesis material 13 is preferably framed at its ends by a stent framework 11 in order to give the vascular prosthesis 10 a hollow-cylindrical structure.

The prosthesis material 13 has three fenestration-cuts 16 in this figure. These are U-shaped or V-shaped and have a different cut length. The length of the cut preferably depends on the diameter of the side branches of the main vessel. If the vascular prosthesis 10 has a second vascular prosthesis which can be released via the flap-like access to form a side arm vascular prosthesis, the cut length is determined by the corresponding diameter of the second vascular prosthesis. If the second vascular prosthesis has a small diameter, the cut length of the fenestration-cut 16 is correspondingly short.

In FIG. 1, "U" refers to an exemplary circumferential section formed by the two meandering stent springs/stent rings $12^{II}$ and $12^{III}$ arranged one behind the other. Accordingly, one boundary of the circumferential section is the course of the stent spring $12^{II}$, the other boundary is formed by the course of the stent spring $12^{III}$.

Depending on the vessel into which the intraluminal vascular prosthesis 10 is to be implanted, it may be necessary for the vascular prosthesis 10 to have several fenestration-cuts 16, especially if the vessel has several branching vessels. In a preferred embodiment, the intraluminal vascular prosthesis 10 has at least as many fenestration-cuts 16 as there are side branches in the region which is to be bridged by the vascular prosthesis 10. The branching side arms of the vessels can be supplied by a second vascular prosthesis, which is placed through the fenestration-cuts 16, or by simply opening the flaps. For this purpose, the vascular prosthesis 10 is implanted in the vessel in such a way that the flap-like access lies directly adjacent to/over the off-branching side arm.

Figure 2:
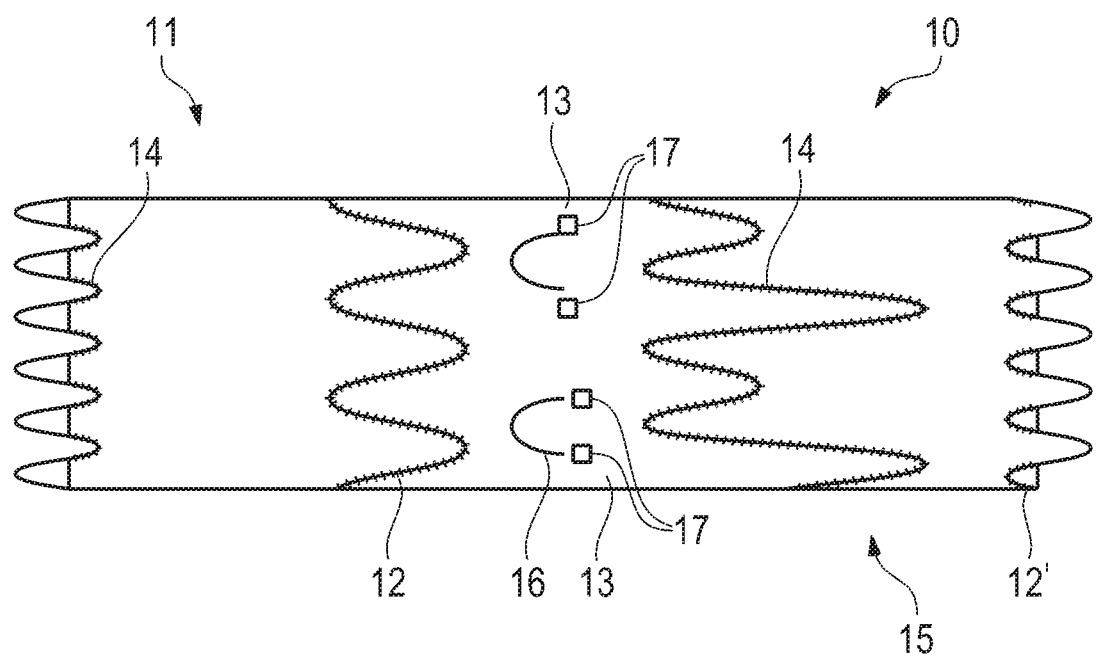
FIG. 2 shows a second schematic view of an intraluminal vascular prosthesis according to the invention.

FIG. 2 shows a second schematic view of an intraluminal vascular prosthesis 10 according to the invention. Here, a complete vascular prosthesis 10 is shown, and not, as in FIG. 1, only a detail of a vascular prosthesis 10. The vascular prosthesis 10 shown has four stent springs 12, which are at least partially secured to the prosthesis material 13 via a seam 14. The stent springs 12 have different amplitudes in this embodiment. The shape of the stent springs 12 depends in particular on the nature of the vessel into which the vascular prosthesis 10 is to be implanted. Particularly stiff vascular prostheses 10 preferably have a large number of stent springs 12, which are preferably connected to each other to form a net-like structure. Less rigid vascular prostheses that can be used for example for thin-walled vessels preferably have stent springs 12 with larger amplitudes. Furthermore, the individual stent springs 12 in this embodiment are mounted to the prosthesis material 13 at a distance from each other.

In this figure, the intraluminal vascular prosthesis 10 has two fenestration-cuts 16. These are located in a region in prosthesis material 13 which is delimited by two stent springs 12. The fenestration-cuts 16 each have a marker 17 at their respective ends of the cut. This marker 17 contains or consists entirely of radiopaque material so that the position of the vascular prosthesis 10 and in particular of the fenestration-cuts 16 in the vessel can be determined during the implantation of the vascular prosthesis 10.

Figure 3:
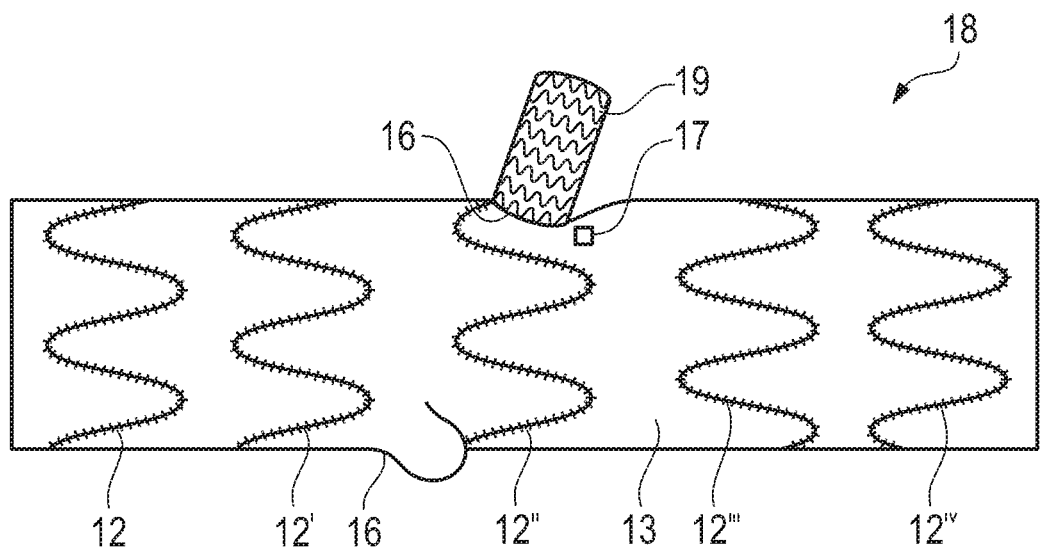
FIG. 3 shows a schematic view of a detail of an intraluminal vascular prosthesis according to the invention with an inserted hollow-cylindrical side body.

FIG. 3 shows a schematic view of a detail of an intraluminal vascular prosthesis 18 according to the invention, with an inserted hollow-cylindrical side body 19. The vascular prosthesis 18 shown in FIG. 3 is substantially similar to the vascular prosthesis 10 shown in FIG. 1. The vascular prosthesis 18 has two fenestration-cuts 16, with one of the flap-like accesses being opened outwardly, and with the other having an additional side body formed by a second vascular prosthesis 19 there through. Off-branching side vessels can be supplied both, i.e. by the opened flap-like access and via the side body.

In this figure, the side body, or the second vascular prosthesis 19, is formed as a covered vascular prosthesis. Other hollow-cylindrical vascular prostheses are also possible, e.g. vascular prostheses without prosthesis material, self-expandable vascular prostheses, balloon-expandable vascular prostheses, etc.

Figure 4:
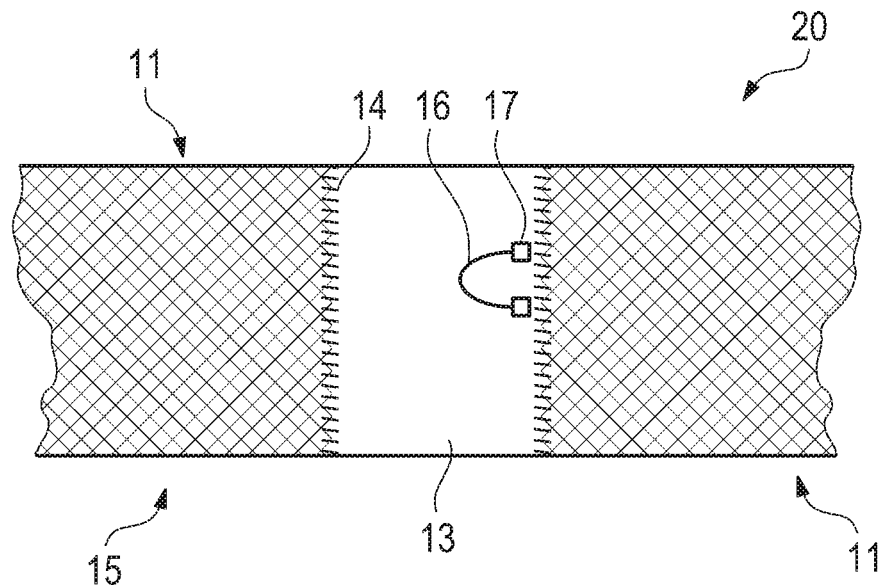
FIG. 4 shows a further schematic view of a detail of an intraluminal vascular prosthesis according to the invention.

FIG. 4 shows a further schematic view of a detail of an intraluminal vascular prosthesis 20 according to the invention. It has two stent frameworks 11, each with a mesh-like or net-like shape. The stent framework 11 is connected to the prosthesis material 13 by a seam 14. In this figure, the stent framework 11 is not covered with prosthetic material 13 as it is shown in FIGS. 1 to 3. The stent framework 11 and the prosthesis material 13, together, form a hollow-cylindrical body 15.

The vascular prosthesis 20 has a fenestration-cut 16 in the prosthesis material 13, which has a marker 17 at each of the ends of the cut.

According to an embodiment not shown in the figures, the stent framework 11 of the vascular prosthesis according to the invention can have any known form of stent elements 12. The stent elements 12 can be self-expanding or balloon-expandable, made of stent springs, stent rings, stent meshes and the like. If the individual stent elements 12 are not interconnected, the stent framework 11 comprises a prosthesis material 13 to form a hollow-cylindrical body 15. In this case, the prosthesis material 13 serves as a connection between the individual stent elements 12. Thus, the vascular prosthesis according to the invention has at least partially a prosthesis material 13 which, for example, is connected or sewn to a continuous stent framework 11 or has at least partially individual stent elements 12 and is connected or sewn to these.

What is claimed is:

1. An intraluminal vascular prosthesis configured for implantation into a blood vessel, with a stent framework and a prosthesis material secured onto the stent framework, wherein the vascular prosthesis has a hollow-cylindrical body with a lumen passing there through and a circumferentially closed jacket, wherein at least one substantially U-shaped or V-shaped fenestration-cut in the prosthesis material of the vascular prosthesis is provided as an outwardly opening flap, wherein the flap opens outwardly away from the lumen of the hollow-cylindrical body, which flap is dimensioned and formed to receive at least one side branch for access to the lumen of the vascular prosthesis, wherein the vascular prosthesis includes fenestration-cuts dispersed on the vascular prosthesis as separate openings into the lumen and is configured to be placed in a blood vessel having fewer side vessels than a number of fenestration-cuts on the vascular prosthesis.

2. The intraluminal vascular prosthesis according to claim 1, wherein the intraluminal vascular prosthesis includes up to eight additional fenestration-cuts on at least one circumferential portion.

3. The intraluminal vascular prosthesis according to claim 1, wherein the stent framework of the intraluminal vascular prosthesis is made of rings of meandering circumferential struts arranged in a longitudinal direction, but not connected to one another.

4. The intraluminal vascular prosthesis according to claim 1, wherein the stent framework extends over an entire length of the vascular prosthesis.

5. The intraluminal vascular prosthesis according to claim 1, wherein a respective stent ring at a first and/or a second end of the vascular prosthesis is provided.

6. The intraluminal vascular prosthesis according to claim 1, wherein the at least one fenestration-cut has a cut length of between 2 mm to 10 mm.

7. The intraluminal vascular prosthesis according to claim 1, wherein when a plurality of the at least one substantially U-shaped or V-shaped fenestration-cuts are present, their cuts have the same or different lengths.

8. The intraluminal vascular prosthesis according to claim 1, wherein the intraluminal vascular prosthesis further has, in addition to the hollow-cylindrical body, at least one hollow-cylindrical side body as the at least one side branch.

9. The intraluminal vascular prosthesis according to claim 1, wherein a marker is located on the intraluminal vascular prosthesis, which marker contains a radiopaque material or is made entirely of radiopaque material, wherein the marker is provided at end points of the at least one fenestration-cut and/or along the fenestration-cut.

10. The intraluminal vascular prosthesis according to claim 1, wherein flap access is formable for the at least one side branch extending inwards into the lumen of the vascular prosthesis and/or outwards from the lumen of the vascular prosthesis.

11. The intraluminal vascular prosthesis according to claim 1, wherein a respective stent ring at a first and/or a second end of the vascular prosthesis is provided and is connected to the stent framework.

12. The intraluminal vascular prosthesis according to claim 1, wherein the at least one fenestration-cut has a cut length of between 5 mm and 7 mm.

13. The intraluminal vascular prosthesis according to claim 1, wherein the intraluminal vascular prosthesis further has, in addition to the hollow-cylindrical body, at least one hollow-cylindrical side body, which is formed by a second vascular prosthesis and which is connectable to the vascular prosthesis via a flap access.

14. An intraluminal vascular prosthesis configured for implantation into a blood vessel comprising:
a stent framework with a prosthesis material secured onto the stent framework, wherein the vascular prosthesis has a hollow-cylindrical body with a lumen passing therethrough and a circumferentially closed jacket, and
one or more substantially U-shaped or V-shaped fenestrations which are cut in the prosthesis material of the vascular prosthesis and provide correspondingly shaped respective outwardly opening flaps, the outwardly opening flaps dimensioned and formed to receive at least one side branch for access to the lumen of the vascular prosthesis, wherein the vascular prosthesis includes fenestrations dispersed on the vascular prosthesis as separate openings into the lumen and is configured to be placed in a blood vessel having fewer side vessels than a number of fenestrations on the vascular prosthesis.

* * * * *